(12) United States Patent
Carfagna, Jr.

(10) Patent No.: US 9,227,128 B1
(45) Date of Patent: Jan. 5, 2016

(54) SYSTEMS AND METHODS FOR VISUALIZING AND ANALYZING IMPACT FORCES

(71) Applicant: Richard Carfagna, Jr., N. Andover, MA (US)

(72) Inventor: Richard Carfagna, Jr., N. Andover, MA (US)

(*) Notice: Subject to any disclaimer, the term of this patent is extended or adjusted under 35 U.S.C. 154(b) by 0 days.

(21) Appl. No.: 14/624,520

(22) Filed: Feb. 17, 2015

Related U.S. Application Data

(63) Continuation of application No. 13/359,486, filed on Jan. 26, 2012, now abandoned.

(60) Provisional application No. 61/436,468, filed on Jan. 26, 2011.

(51) Int. Cl.
    A63B 69/32 (2006.01)
    A63B 24/00 (2006.01)
    A63B 69/00 (2006.01)

(52) U.S. Cl.
    CPC .............. *A63B 69/32* (2013.01); *A63B 24/0062* (2013.01); *A63B 24/0087* (2013.01); *A63B 69/004* (2013.01); *A63B 2220/51* (2013.01); *A63B 2220/53* (2013.01)

(58) Field of Classification Search
    CPC .. A63B 69/32; A63B 69/004; A63B 24/0062; A63B 24/0087; A63B 2220/51; A63B 2220/53
    See application file for complete search history.

(56) References Cited

U.S. PATENT DOCUMENTS

| | | | |
|---|---|---|---|
| 4,534,557 A | 8/1985 | Bigelow et al. | |
| 4,721,302 A | 1/1988 | Murphy | |
| 4,761,005 A * | 8/1988 | French | A63B 24/0021 273/454 |
| 4,941,660 A | 7/1990 | Winn et al. | |
| D377,201 S | 1/1997 | Howard | |
| 5,605,336 A | 2/1997 | Gaoiran et al. | |
| 5,733,193 A | 3/1998 | Allard et al. | |
| 5,803,877 A | 9/1998 | Franey | |
| 6,280,351 B1 | 8/2001 | Wong | |
| 6,397,151 B1 | 5/2002 | Yamagishi et al. | |
| 6,925,851 B2 | 8/2005 | Reinbold et al. | |
| 7,308,818 B2 | 12/2007 | Considine et al. | |
| 7,909,749 B2 | 3/2011 | Sheedy | |
| 2003/0216228 A1* | 11/2003 | Rast | A63B 21/0087 482/84 |
| 2003/0217582 A1* | 11/2003 | Reinbold | A63B 69/32 73/12.09 |
| 2005/0266967 A1* | 12/2005 | Considine | A63B 69/20 482/84 |
| 2006/0201580 A1* | 9/2006 | Kang | A63B 69/00 144/195.5 |
| 2007/0015637 A1 | 1/2007 | Penner et al. | |
| 2007/0087911 A1* | 4/2007 | Ghim | A63B 69/20 482/84 |
| 2008/0125293 A1* | 5/2008 | Ng | A63B 69/32 482/84 |
| 2008/0174548 A1* | 7/2008 | Jones | A63B 24/0062 345/156 |
| 2008/0215285 A1* | 9/2008 | Bucar | A63B 69/201 702/139 |
| 2009/0293587 A1* | 12/2009 | Mages | A63B 69/004 73/12.01 |

(Continued)

*Primary Examiner* — Loan H Thanh
*Assistant Examiner* — Sundhara Ganesan
(74) *Attorney, Agent, or Firm* — Underwood & Associates, LLC

(57) ABSTRACT

Impact force feedback systems (IFFS) and methods for their use are described. The IFFS can measure and display raw or calculated data relating to impact force imparted to an object by a user. In a preferred embodiment the IFFS can be implemented in a boxing or martial arts configuration, where impact force(s) resulting from punches, kicks, and the like are displayed to a user.

20 Claims, 14 Drawing Sheets

(56) References Cited

U.S. PATENT DOCUMENTS

| | | | |
|---|---|---|---|
| 2010/0130329 A1* | 5/2010 | Sullivan | A63B 69/004 482/4 |
| 2010/0144414 A1* | 6/2010 | Edis | A63B 24/0006 463/8 |
| 2011/0111924 A1* | 5/2011 | Jones | A63B 69/32 482/8 |
| 2011/0130183 A1* | 6/2011 | Pelletter | A63B 69/004 463/7 |
| 2011/0159939 A1* | 6/2011 | Lin | A63B 69/004 463/8 |
| 2011/0172060 A1* | 7/2011 | Morales | A63B 69/004 482/8 |
| 2012/0053016 A1* | 3/2012 | Williamson | A63B 24/0062 482/8 |
| 2012/0198593 A1* | 8/2012 | Beck | F41H 1/02 2/2.5 |

* cited by examiner

SYSTEMS AND METHODS FOR VISUALIZING AND ANALYZING IMPACT FORCES

CROSS REFERENCE TO RELATED APPLICATIONS

Continuation of U.S. application Ser. No. 13/359,486, filed Jan. 26, 2012, now abandoned, which claims priority under 35 U.S.C. §119(e) of U.S. Application No. 61/436,468, filed Jan. 26, 2011 by Richard Carfagna Jr., entitled "Systems and Methods for Visualizing and Analyzing Impact Forces," and is incorporated by reference herein in its entirety for all purposes.

TECHNICAL FIELD

This disclosure relates to systems and methods for measuring and displaying impact forces in a variety of combinations and implementations. In preferred embodiments, systems and methods are disclosed for correlating impact force data from punches, kicks, and other strikes, and displaying those and related data on a display screen.

BACKGROUND

Athletes often train in ways that mimic the play of their particular sport during competition. For example, runners can improve their racing performance by engaging in endurance and sprint training; baseball pitchers practice repetitive pitching motions to build muscle memory and perfect their pitching style; rowers may practice on a machine constructed to mimic the confines of a rowboat so that a participant can train in an indoor facility. Exercise training is a popular activity that not only increases performance in a particular sport, but also provides improved health, teamwork, and camaraderie.

Sparring is one of the oldest known physical sport activities that pit strength, endurance, tactical knowledge, and other elements between two or more opponents. Sparring is frequently practiced in martial arts and boxing training regimens. However, some practitioners also enjoy sparring alone by practicing kicks, punches, and other strikes against various types of sporting equipment, such as punching bags.

SUMMARY

In one general aspect, a system capable of providing data analysis of impact force(s) is described. Impact force can be force generated by a kick or punch against a surface, such as the surface of a punching bag, pad, or other piece of equipment.

In one general aspect, an impact force feedback system (IFFS) is disclosed. The IFFS includes one or more impact force sensors in communication with a central processing system capable of outputting impact force data to a visualization system. In one embodiment, impact force data is generated by a user striking a sensor, e.g., during boxing or martial arts training. The impact force data is sent to a computer-implemented control module capable of performing statistical analysis of the impact force data; the control module can then send the data to a display device. In one embodiment, the user can select what data is displayed through an interface that allows selection of various statistical output, such as average strike force, strikes per round, combination strikes to multiple sensors, etc.

In one general aspect, an impact force feedback system is disclosed. The impact force feedback system includes a control module capable of measuring, in absolute units, a strike impact force imparted to one of a plurality of flexible impact force sensors, wherein the control module is configured to communicate the strike impact force measurements to a display device for feedback purposes, wherein the display device is capable of displaying the strike impact force measurements according to a predefined user preference. The plurality of flexible impact force sensors are arranged to substantially mimic one or more parts of a human anatomy and fixed as such on or within a mountable, flexible striking surface.

In one embodiment, the impact force sensor is a force-sensing resistor.

In one embodiment, the striking surface includes a mat having a first layer of flexible, resilient material, and the plurality of flexible impact force sensors are affixed to the first layer in an arrangement that mimics one or more parts of a human anatomy. In one such embodiment, the mat includes a second layer of flexible, resilient material, which may be the same or different material as the first layer; wherein the plurality of flexible impact force sensors are juxtaposed between the first and said second layer in an arrangement that mimics one or more parts of a human anatomy.

In one embodiment, the mountable, flexible striking surface is configured to be adapted to a punching bag having a substantially cylindrical shape.

In one embodiment, the control module is capable of performing analyses of strike impact force measurements according to pre-defined user preference. In one such embodiment, the pre-defined user preference is one or more of: strike force to an impact force sensor in absolute units, strike force to an impact force sensor averaged over a selected period of time, and strike forces to multiple impact force sensors.

In one embodiment, the impact force feedback system further includes a physiological sensor capable of transmitting physiological measurements to the control module. The physiological measurements can include one or more of heart rate, blood pressure, blood oxygenation, or temperature. The control module is further capable of causing the physiological measurements to be displayed on the display.

In one embodiment, the data communication comprises using a wireless data transfer protocol.

In one embodiment, the display device is a touch-screen display device. The touch-screen display device includes an active-touch area for receiving a user input, and the user input is capable of being transmitted to the control module to control, activate, or cause a desired computer-executable instruction to occur.

In one embodiment, the control module is capable of storing software instructions for leading an exercise routine. One or more aspects of the exercise routine can be communicated to a user through display of workout instructions on the display device, through auditory commands, or both. In one such embodiment, an exercise routine includes one or more of: executing a pre-defined number of strikes in a pre-defined time period to one or more of the plurality of impact force sensors; executing a pre-defined number of strikes delivered with a pre-defined threshold of force; and executing random strikes as kicks or punches until a pre-defined physiological threshold is achieved. In one such embodiment, the control module is capable of, and configured to send and receive electronic data on a network. The control module is further capable of receiving media communication from a remote user and causing the media to be shown on the display. In one such embodiment, the media is video.

In one embodiment, the impact force feedback system further includes a touch sensor affixed to the striking surface and capable of communicating with the control module through electronic signals to allow a user to interface with, or control the software instructions for leading an exercise routine. In one such embodiment, the exercise routine is a boxing, martial art, or mixed martial arts routine.

In one general aspect, a method for providing a customized exercise routine is disclosed. The method includes identifying a sequence of one or more strikes to be delivered by a practitioner to one or more target strike zones of the impact force feedback system described above. The method further includes storing the sequence as software instructions in a format that allows the control module to communicate the sequence to the practitioner through the display of workout instructions on the display device, through auditory commands, or both.

In one general aspect, a system for practicing punches, kicks or other strikes is disclosed. The system includes first and second force-sensing resistors arranged on a striking surface so as to mimic, along with other force-sensing resistors, all or part of a human form. The first and second force-sensing resistors are also configured to transmit a measure of striking force when punched, kicked, or otherwise struck by a practitioner to a control module. The control module is capable of receiving the striking force data and displaying the data in human-readable form, in units of absolute measurement, on a display device. The first force sensing resistor is capable of measuring a strike force imparted thereto, even when a substantially concurrent strike force is delivered to the second force-sensing resistor.

In one embodiment, the first force sensing resistor is capable of measuring a strike force that is independent of a strike force being delivered to the second force-sensing resistor or to any other area on the striking surface other than the first force sensing resistor.

In one embodiment, the first and said second force-sensing resistors are arranged to be substantially adjacent and mimic, in whole or in part, a human anatomical feature.

Certain advantages of the systems and methods include calculation of both simple and complex impact force statistical data; an intuitive interface allowing users to realize variable levels of statistical granularity; visual and auditory feedback relating to impact force data and work-out routines; and the ability to navigate software menus and statistical data, and control aspects of a software control program using a gloved hand; among others.

The foregoing summary is illustrative only and is not intended to be in any way limiting. In addition to the illustrative aspects, embodiments, and features described above, further aspects, embodiments, and features will become apparent by reference to the drawings and the following detailed description and claims.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

DESCRIPTION OF DRAWINGS

The present embodiments are illustrated by way of example and not limitations in the figures of the accompanying drawings in which like references indicate similar elements, and in which.

DETAILED DESCRIPTION OF ILLUSTRATIVE EMBODIMENTS

In general, this disclosure describes systems and methods for measuring, analyzing, storing and/or recording, and displaying impact force data.

Figure 1A:
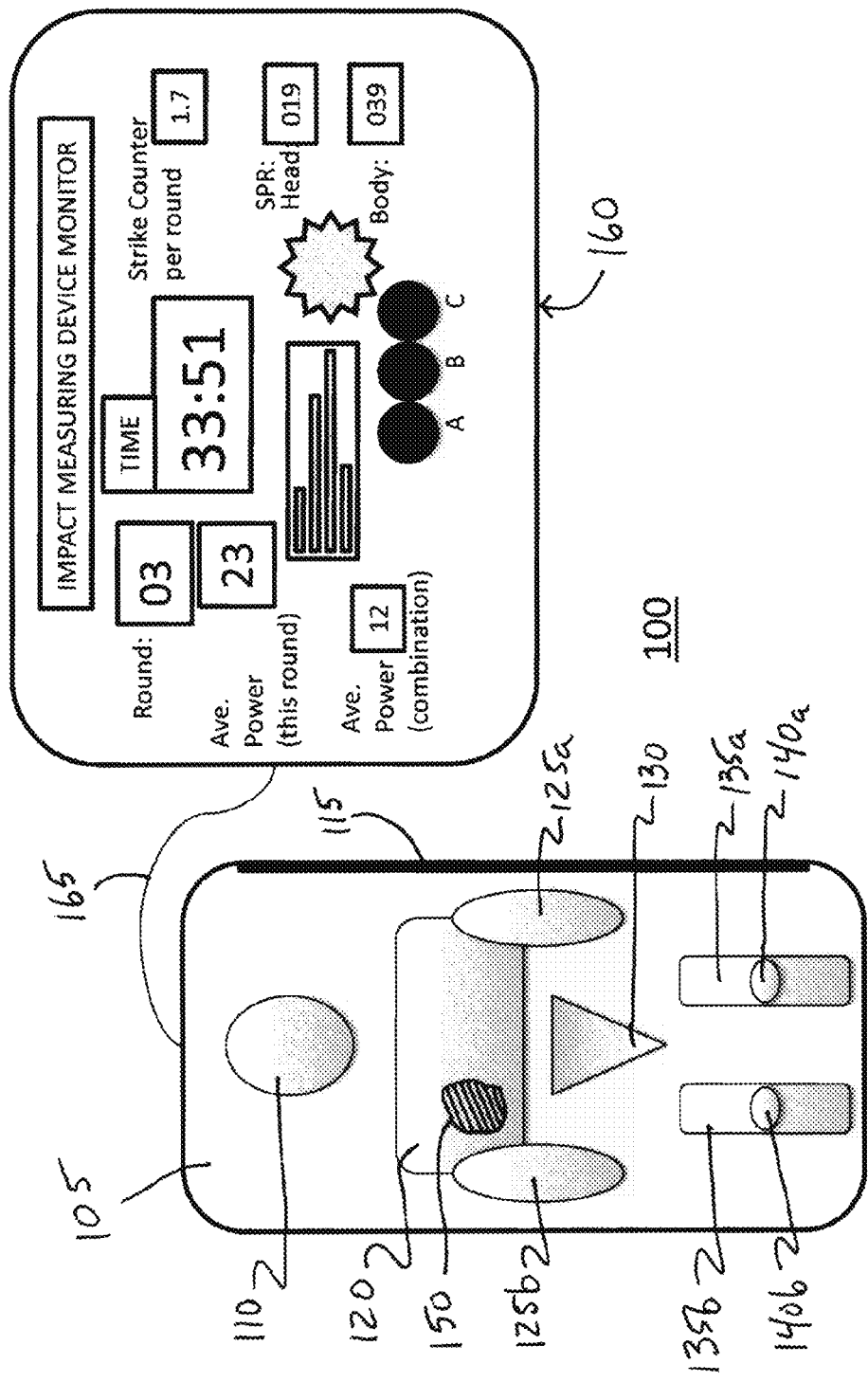
FIG. 1A is a system for generating, analyzing, and displaying impact force data, according to one embodiment.

FIG. 1A shows an impact force feedback system (IFFS) 100 according to one embodiment. The IFFS 100 includes a mat 105 having one or more sensors, e.g., head sensor 110, torso sensor 120, arm sensors 125a, 125b, etc., which, in this embodiment are positioned to collectively mimic the human anatomy. The sensors can be configured to measure and transmit impact force data when they are struck, e.g., by a punch or a kick, to a control module (not shown in FIG. 1A for clarity). The control module can be configured to receive the impact force data, perform any analysis or calculations on the data (which may be defined by, or chosen by the user as described in greater detail below), and transmit those data to a display 160 capable of displaying the data in a preferred manner. For example, the control module can calculate average punching or kicking force or power, the number of strikes delivered to the sensors per round (where a "round" is a defined amount of time, typically used in sparring and work-out sessions), the ratio of head to body punches delivered, and other calculations, some of which are described below. Many other variations and alternatives of the systems and methods shown and described herein will occur to those skilled in the art.

In one embodiment, the mat 105 can be made of one or more layers of material to contain or support the sensors, leads, and other electronic components that transmit impact data from the various sensors to the control module. In a preferred embodiment, the mat 105 is made from a resilient material having a surface that can withstand repeated blows by a boxer or martial artist without significant degradation to the material or seams. Preferred mat 105 materials include, without limitation, leathers, canvas, and other materials commonly used as the outer striking surface of so-called "punching bags" that boxers and martial artists alike will recognize.

It will be understood, however, that the 105 mat can include, or be composed of any type of material capable of having a sensor attached thereto or therein. FIG. 1A shows the mat 105 in a flat orientation for clarity, however, it will be understood that the mat 105 can be flexible, and can wrap around objects as described below.

Figure 1B:
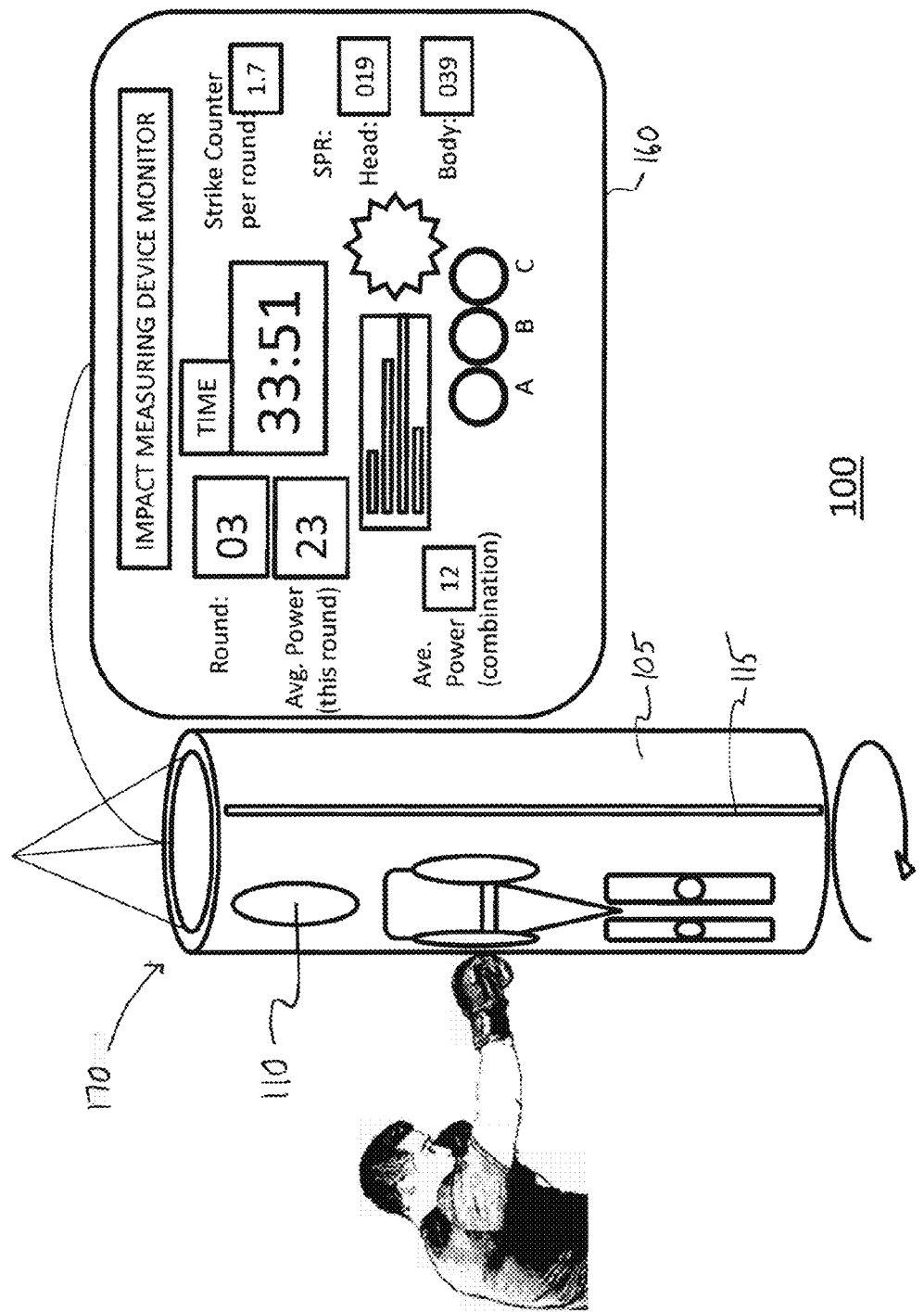
FIG. 1B shows the system of FIG. 1A wrapped around a punching bag, according to one embodiment.

Referring now to FIG. 1B, in one embodiment, the mat 105 is capable of being wrapped around the exterior of a cylindrical object such as a punching bag 170 as illustrated by the arrow. It will be understood that the mat 105 can be secured about the exterior periphery of the punching bag using a variety of methods. In this embodiment, a length of hook-and-loop fastener 115 is used so that the user may easily don and doff the mat 105 about the punching bag 170. In this embodiment, one portion of the mat 105 includes a strip of hook-side fastener and another, opposite-side portion includes the loop-side fastener (not shown in FIG. 1). Suitable hook-and-loop fasteners include those manufactured under the Velcro brand, among others. Other methods can be used to secure the mat 105 about a punching bag, including, e.g., ties, bands, metal and plastic hooks and loops, and tongue-and-groove-style fastening strips. In one embodiment, the mat 105 can be designed to snugly fit around a punching bag, wherein frictional forces keep the mat 105 in place relative to the bag 170.

In general, as disclosed above, the mat 105 can include one or more sensors (e.g. head sensor 110) that measures impact or "strike" forces that occur when a user kicks, punches, or otherwise strikes the sensor. Without limitation, suitable sensors can include one or more of: accelerometers, dynamometers, magnetic-based sensors, optical-based sensors, force-sensing resistors, capacitive resistors, load cells, or other sensors that can measure impact force with a desired degree of accuracy. Exemplary sensors that can be used in any embodiment described herein include force sensors sold under the FlexiForce brand (Tekscan, Inc., South Boston, Mass., USA) and force sensing resistors provided by Interlink Electronics, Inc., Camarillo, Calif., USA. The size and shape of the sensors can be selected for the intended use. For example, large, life-like sensors can be used to imitate the anatomy of a human subject; however, smaller sensors can be used in so-called "focus" mitts and other equipment. Small sensors can be used, for example, to develop the practitioner's accuracy. In the exemplary embodiment of FIGS. 1A and 1B, the mat 105 includes a head (110), torso (120), left and right arms (125a, 125b, respectively), groin (130), left and right legs (135a, 135b, respectively), and right and left kneecaps (140a, 140b, respectively).

In one embodiment, a sensor can measure impact forces independently or in combination with one or more other sensors. For example, a strike to the kneecap area can trigger a force measurement from kneecap sensor 140a and leg sensor 135a. The extent to which a secondary sensor (e.g., the leg sensor 135a in this example) receives impact force resulting from a strike to a primary sensor (e.g., the kneecap sensor 140a) can be controlled by programmatic methods as described below, or through selection and use of sensors capable of recording force independently. In one embodiment, suitable sensors can be chosen to reduce "noise" in measured data, wherein the sensors will not record a force measurement unless they are struck directly. This approach can reduce false measurement of a first sensor, for example, when the practitioner strikes other near-by sensors or other places on the mat that are not in direct contact with the first sensor. Alternatively, or in combination, the same can be accomplished by placing pads or other force-attenuating means between primary and secondary sensors (e.g., between kneecap 140a and leg 135a sensors), wherein the pads or other force-attenuating means provides a calibrated force-reducing factor between primary and secondary sensors. Such functionality can be useful in training, as the measured forces from multiple sensors can supply feedback to the practitioner that mimics a real-life infliction of strike force.

In one embodiment, a sensor, e.g., torso sensor 120 can measure total impact force across its entire area, or, in some embodiments, a sensor can be configured to provide local impact force measurements (i.e., "mapped" forces) within one region of its total area. To provide such functionality, in one embodiment, a sensor (e.g., torso sensor 120) can include a plurality of smaller sensors, which can be mapped throughout the total area of the region. "Mapped" implies that the position of any smaller sensors within a larger sensor are known, and that the smaller sensors are capable of transmitting measured forces independently. For example, referring to FIG. 1A, a strike to the cross-hatched portion 150 of the torso sensor 120 can be measured, analyzed, and recorded as a strike to the right side of the torso. Using a mapped array of force-measuring components can allow recordation of strikes to any desired target or area, e.g., right, center, or middle strikes to the sensors. Similarly, the head sensor 110 can include a mapped array of sensors to distinguish strikes to lower and upper portions of the sensor, including anatomical areas such as the eyes, ears, nose, mouth, etc.

In one embodiment, strike zones can be defined that correspond to a real opponent's so-called "weak spots" so that the user can specifically target those areas in training. For example, if a boxer's opponent has a known recent injury to his left elbow, it may be tactically advantageous to the boxer to target strikes to the corresponding elbow zone on left arm sensor 125a, in anticipation of a boxing match. In one embodiment, the control module can be programmed to indicate through visual, audible, or other means that the user successfully struck a targeted zone. Furthermore, the control module can be programmed to prompt the user to strike the targeted zones if no such strikes have been detected, or if the strikes are not occurring according to a predetermined (i.e., user-customizable) frequency, for example, at least 10 strikes to the targeted zone per round.

Figure 2:
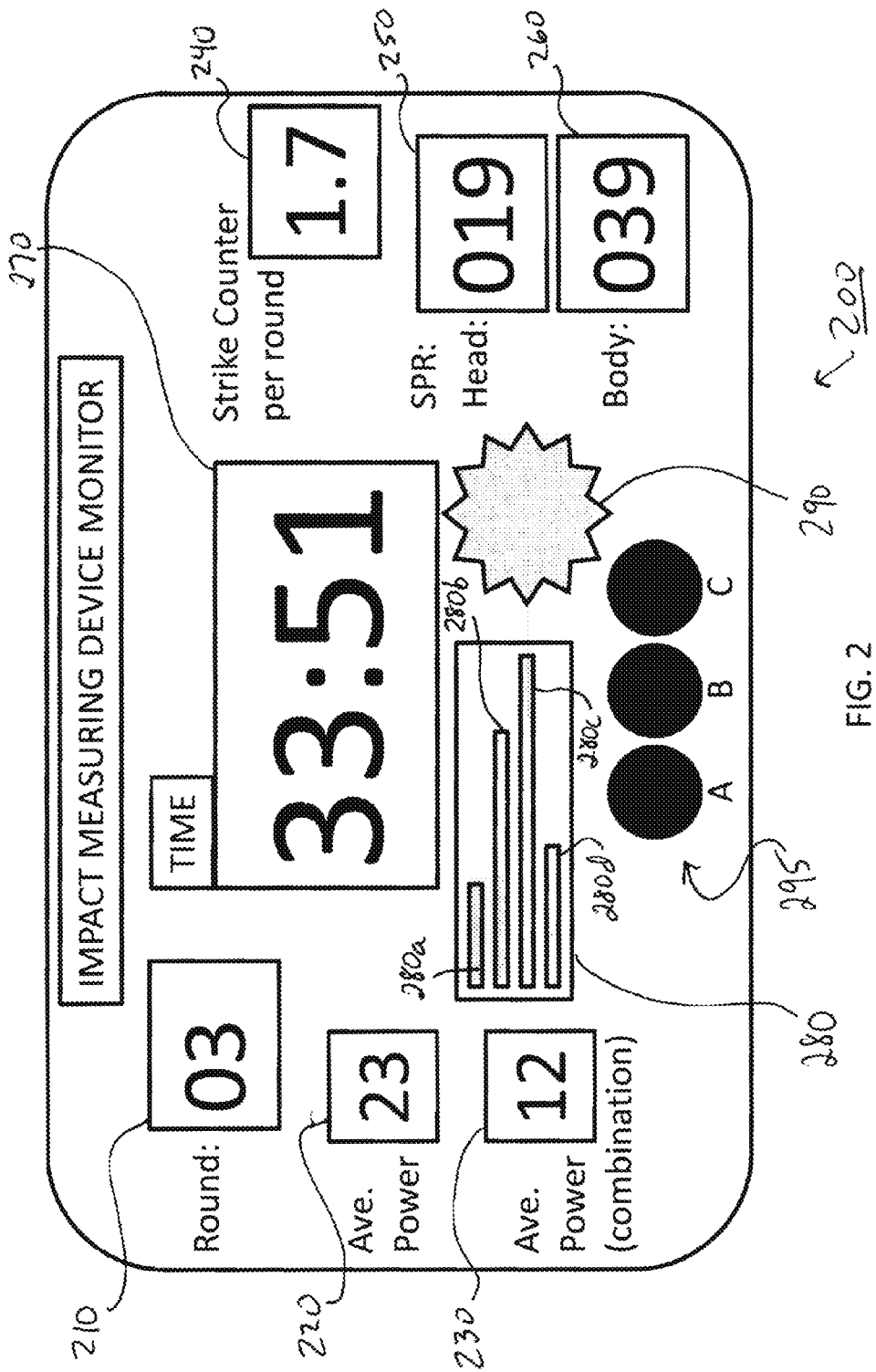
FIG. 2 is an exemplary display screen, according to one embodiment.

Referring now to FIG. 2, a display 200 is shown, according to one embodiment. In general, the display 200 shows data relating to forces imparted to one or more sensors on, or in a mat or other material containing the sensors (e.g., mat 105 in FIG. 1A). In some embodiments, the sensors can transmit force data directly to the display 200, where those data can be displayed; however, in other embodiments, computer hardware, software, and combinations thereof may be used to collect data from the one or more sensors on, or in the mat 105, and condition or format those data such that the display 200 is capable of showing impact force measurements. The display 200 can be an LCD screen, for example, or any other type of electronic device capable of receiving and displaying data and other information to a user. In one embodiment, the display 200 is a display screen on a personal computing tablet such one sold under the iPad brand by Apple, Inc.

In one embodiment, a control module (not shown in FIG. 2) can receive impact force data from the one or more mat sensors. The control module can include computer hardware, software, networking devices, or combinations thereof so as to be in full data communication with the one or more mat sensors. The control module can send (receive) data to (from) the display 200 using a wired or wireless connection. In one example, the control module can communicate with the display 200 via a wireless Bluetooth connection. In another example, the control module may be integral with the display 200. The display 200 can be fully customizable by a user, programmer, or other person skilled in the art to display desired impact force measurements and other data, such as timers and the like, which are described in greater detail herein. In the embodiment of FIG. 2, the display 200 includes a 'round' indicator 210, an 'average power' indicator 220, an 'average power (combination)' indicator 230, a 'strike counter per round' indicator 240, and a 'strike per round (head)' 250 and 'strike per round (body)' 260 indicator for strikes corresponding to a head and body sensor, respectively, e.g., head sensor 110 and torso sensor 120 as shown in FIG. 1A. The display 200 in FIG. 2 also includes a 'time' indicator 270 that can show, e.g., the amount of elapsed time that the user has been practicing, the amount of time left in a practice round, or other alternatives.

In this embodiment, display 200 further includes an 'intensity' display 280. The intensity display 280 includes status bars 280a-d, each of which can be capable of indicating a workout intensity measurement or progress toward a workout goal, e.g., by varying the length of the appropriate bar in the display 280. For example, in one embodiment, a user can don one or more devices that measure physiological vital signs, such as respiratory rate, heart rate, blood-oxygen saturation, etc. The vital sign data can be sent to the control module, where it can be analyzed, compared to pre-determined workout goal data, and the results of the comparison can be displayed in the intensity display 280. The intensity display 280 can also show substantially real-time physiological data, e.g., bar 280a can correlate to heart rate, bar 280b can correlate to respiratory rate, bar 280c can correlate to blood-oxygen saturation, and bar 280d can correlate with blood pressure measurements. Those skilled in the art of computer hardware and software programming and design will appreciate the vast number of alternative data and displays that can be incorporated, e.g., calories burned, core temperature, endurance, etc.

In another embodiment, the intensity display 280 can show progress toward certain workout goals that can be pre-loaded into the control module. In this embodiment, the variable-length indicator bars 280a-d can show progress toward, e.g., a preferred number of strikes per round, average power per strike, average power per combination of strikes, etc.

In any of the embodiments described herein, the display 200 can allow the user to receive real-time feedback relating to their workout, sparring goals, and other factors. The type of information displayed on the display 200 can depend on the sport- or style of sport. For example, boxers may wish to know the average force of their punches delivered to the torso area and above. Martial artists, on the other hand, may wish to know detailed power and force delivered when striking any sensor.

Still referring to FIG. 2, the display 200 includes an exemplary master indicator 290. The master indicator 290 can be, e.g., a bright LED or incandescent light and, in some embodiments, can be coupled with an audible annunciator. The master indicator 290 can be activated by pre-programmed triggers to provide additional feedback to the user. For example, a martial artist may wish to improve the speed at which he delivers combination blows to different parts of the body. The user can set a trigger that activates the master indicator 290 when the time between multiple strikes to sensors, e.g., sensors 120 and 130 is less than a predetermined threshold, e.g., 5 seconds. In another example, a trigger can activate the master indicator by delivering a punch or kick to a predetermined sensor at, or above a threshold level of force.

Still referring to FIG. 2, input buttons 295 on the display 200 provide a user interface to programmatic features of an IFFS, e.g., the IFFS 100 in FIG. 1A. In the embodiment of FIG. 2, the display 200 includes three input buttons 295 labeled "A," "B," and "C." These input buttons can be any type of button, switch, or other control mechanism known in the art, including real and virtual control mechanisms (i.e., software-enabled), that allow a user to provide input to a computer program module. The module can be part of an overall software package that enables an IFFS to operate as described herein; e.g., the module can be used to receive user input, navigate menus, answer queries, etc. Such a module(s) is described in greater detail herein. It will be understood that displays in other embodiments can include as many user-input buttons as desired; the number of buttons on a display can be chosen so as to provide an intuitive and useful interface to the programmatic features of an IFFS. In one embodiment, the input buttons 295 are incorporated into a touch-screen display. The buttons can be large enough, and adequately spaced on the display to facilitate being activated with a gloved hand, i.e., they can be of adequate size and spaced apart such that the possibility of touching two or more buttons simultaneously is minimized.

The display 200 can be customized for various sports and training regimens. In some embodiments the contents of the display are entirely digital, to include all markings, indicia, labels, data, and the like. In other embodiments, the contents of the display can include static, substantially permanent indicia; for example, the word "time" in the time indicator 270 can be made a permanent fixture on the display 200, whereas the actual digits corresponding to the timer can be digital.

Figure 3:
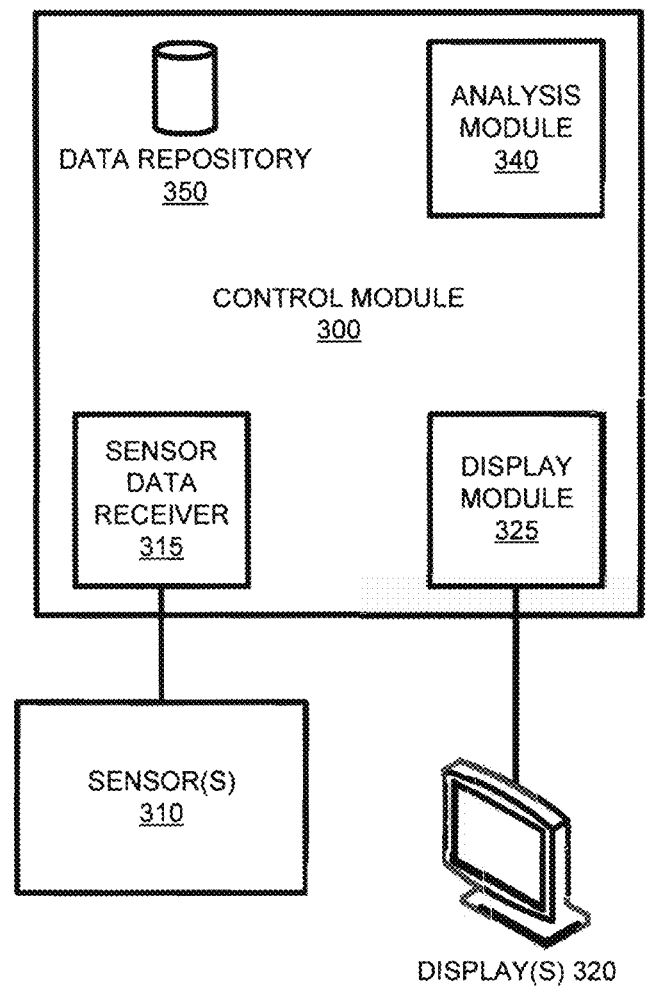
FIG. 3 is a control module, according to one embodiment.

Referring now to FIG. 3, an IFFS control module 300 and exemplary associated peripheral devices are shown, according to one embodiment. The control module 300 can receive signal data from one or more sensors 310, e.g., those sensors described with respect to FIG. 1A, process or analyze the signal data, and send or receive display information to one or more displays 320. In some embodiments, the control module 300 can store data received from the one or more sensors 310 in a data repository 350.

In general, the control module 300 can include computer hardware and software for receiving impact force data from the sensors 310, processing or analyzing those data, if required, formatting those data for display, if required, and performing other functions that may be desirable for a user of an IFFS. Non-limiting examples of such other functions include storing workout routines and preferred round time limits, setting impact force thresholds and comparing those thresholds to actual impact force measurements, etc.

In one embodiment, impact force data can flow from an impact sensor to the control module 300 as follows. As a user strikes one or more sensors 310, a signal can be transmitted from the one or more sensors to the sensor data receiver module 315. The signal can be a wireless digital signal, for example, or a hard-wired electronic signal. The sensor data receiver module 315 can be, e.g., a wired- or wireless communications device capable of receiving signals sent by the one or more sensors 310. One non-limiting example of a sensor data receiver is a Bluetooth wireless receiver. In some embodiments, the sensor data receiver module 315 can perform calculations to convert the electrical signal to a force measurement, i.e., a measurement having units of force, such as Newtons (N) or pounds (lb.). In some embodiments the sensors 310 can have integrated electronics that perform such calculations and send the resultant data to the sensor data receiver 315.

In one embodiment, impact force data from the sensor data receiver 315 can be passed to the analysis module 340. In some embodiments, the processed signal data can also be stored in the data repository 350 for analysis. The analysis module 340 can perform the calculations and functions necessary to display desired impact force data on the display 320. In some cases where the user wishes to view raw data, e.g., number of strikes, impact force of strikes, etc., the analysis module 340 can receive data from the sensor data receiver 315 and pass it directly to the display module 325. In other cases, however, the analysis module 340 can load software programs from computer memory (not shown in FIG. 3) or the data repository 350 that perform calculations on the impact force data received by the one or more sensors 310. Non-limiting examples of some exemplary analysis module functions include: tracking average force of strikes to one or more sensors (e.g., sensor 110 in FIG. 1A), tracking average striking force of combinations of kicks and punches to one or more sensors, tracking strikes to particular sensors, monitoring for strikes to pre-identified strike zones (e.g., to practice targeting an opponent's weak spots, as discussed above) and other functions. Strike force can be expressed using a desired system of measurement or units, and can be converted to alternative expressions of force, including, but not limited to strength, power, pressure, or other measurements or units.

In one embodiment, the display module 325 can receive output data from the analysis module and send the information to one or more displays 320. The display module 325 can also receive input from one or more displays 320 to perform functions such as selecting and changing software program menus, selecting responses to queries, e.g., "Go for another round?" and overall control of software program functions of the IFFS. Exemplary display modules are known in the art, for example, those display modules used for touch-screen displays and the like.

The control module 300 can be embodied in a computing device, e.g., a personal computer, or, in some embodiments, it can be a stand-alone device having a power source and other ancillary components to provide the IFFS functionality as described herein, including other functionality that will occur to those skilled in the art of computer hardware, software, programming, and similar disciplines.

In some embodiments, the control module 300 can include electronic networking components to communicate wirelessly with one or more sensors 310. For example, the control module 300 can include one or more transceivers to communicate with a transceiver or transmitter located on, or within a sensor. A sensor transmitter can be integrated into an individual sensor, or, alternatively, a single transmitter can send impact force data corresponding to a plurality of sensors, wherein those data are addressed so as to identify the sensor supplying the impact force measurement. In some embodiments, a wireless data transceiver can be incorporated into a sensor data receiver, e.g., sensor data receiver 315.

In general, an IFFS (e.g., IFFS 100 in FIG. 1), and more specifically, a control module of an IFFS, can include executable software allowing customization of data shown on the one or more displays, e.g., display 200 shown in FIG. 2. An IFFS can also include software packages for analyzing impact force and power data received from one or more sensors. Such analysis software packages can store analysis results and also output same to a user, e.g., a trainer. In one embodiment, an IFFS includes the necessary computer hardware, software, and peripheral devices to be capable of sending and receiving data on a network, e.g., the Internet. In such cases, an IFFS can be capable of sending and receiving data using HTML, email, SMS, and other protocols. In one embodiment, a remote user such as a coach can communicate with the IFFS through a network, and vice-versa. This provides the capability for the remote user to load data into the control module of the IFFS for various purposes. In one example, a coach can load a personalized workout routine into a user's IFFS control module from a remote location. This can allow, e.g., one coach to train multiple athletes from a single location. Similarly, when the user completes the personalized workout, the control module can send impact force and other data collected during the workout so that the coach can view and analyze the results. In a related embodiment, an IFFS can include necessary hardware, software, and peripheral devices to enable video and other images to be captured. In one application of such an embodiment, a remote user such as a coach can connect to the IFFS via a network connection and view a user performing a workout on the IFFS. In certain embodiments, the remote user can communicate with the user using, e.g., speakers, video screens, or other devices that will be apparent to those skilled in the art.

In some embodiments, an IFFS can include software for customizing a workout routine that is geared for a particular sport, e.g., customized for boxing, different forms of martial arts, fencing, football, and others. In some embodiments, the software can be customized for a particular art (e.g., boxing) yet also capable to display sensor data in any form, whether they are calculated results of sensor data (e.g., average power per strike) or simply raw data (e.g., an incremental strike counter). In one such example, a workout routine can include prompting the practitioner to execute a series of punches or kicks in a given time interval, to specific target zones (e.g., head, torso, arms, etc.), using specific combinations, etc. The IFFS can be capable of monitoring the practitioner's strikes and whether they correlate with the workout routine; in this manner, the IFFS can be capable of prompting the practitioner to speed up, slow down, use better aim, hit harder or softer, or any combination thereof, and including other prompts.

In one embodiment, an IFFS can perform sensor impact analysis, which can allow users and trainers to analyze data expressed in different ways, e.g., single-data-point or averaged striking-force data. For example, impact analysis data can be used to selectively analyze individual strikes, combinations of strikes, strikes per round, strikes per workout (e.g., strikes per 12-round workout), and other data according to user preference. Other data can include, e.g., number of body strikes, head strikes, and strikes to other body parts; the proportion of straight strikes and hook or uppercut strikes, etc. Analysis of these data and others can allow a user to determine where the practitioner (a boxer, in this example) is strongest and weakest with respect to their fighting discipline or style.

In one example, analysis of impact force data can aid in determining a fighter's stamina; e.g., whether a fighter is significantly weaker in round 6 versus round 1. In another example, such analysis can aid in determining if a fighter changes his tactics after a certain amount of workout time, e.g., by examining proportion of head vs. torso strikes; or, in embodiments where the practitioner's vital signs are being monitored, when the practitioner reaches a certain threshold of physical exertion. Those skilled in the art of software-implemented data manipulation and programming will appreciate the wide variety of data analysis that can be performed and presented, either via a display, or using an interface such as a personal computer. One particular advantage of an IFFS is that practitioners (e.g., professional fighters) and trainers can identify strengths and weaknesses in their style, stamina, strength, and other areas, and make appropriate training adjustments.

Figure 4:
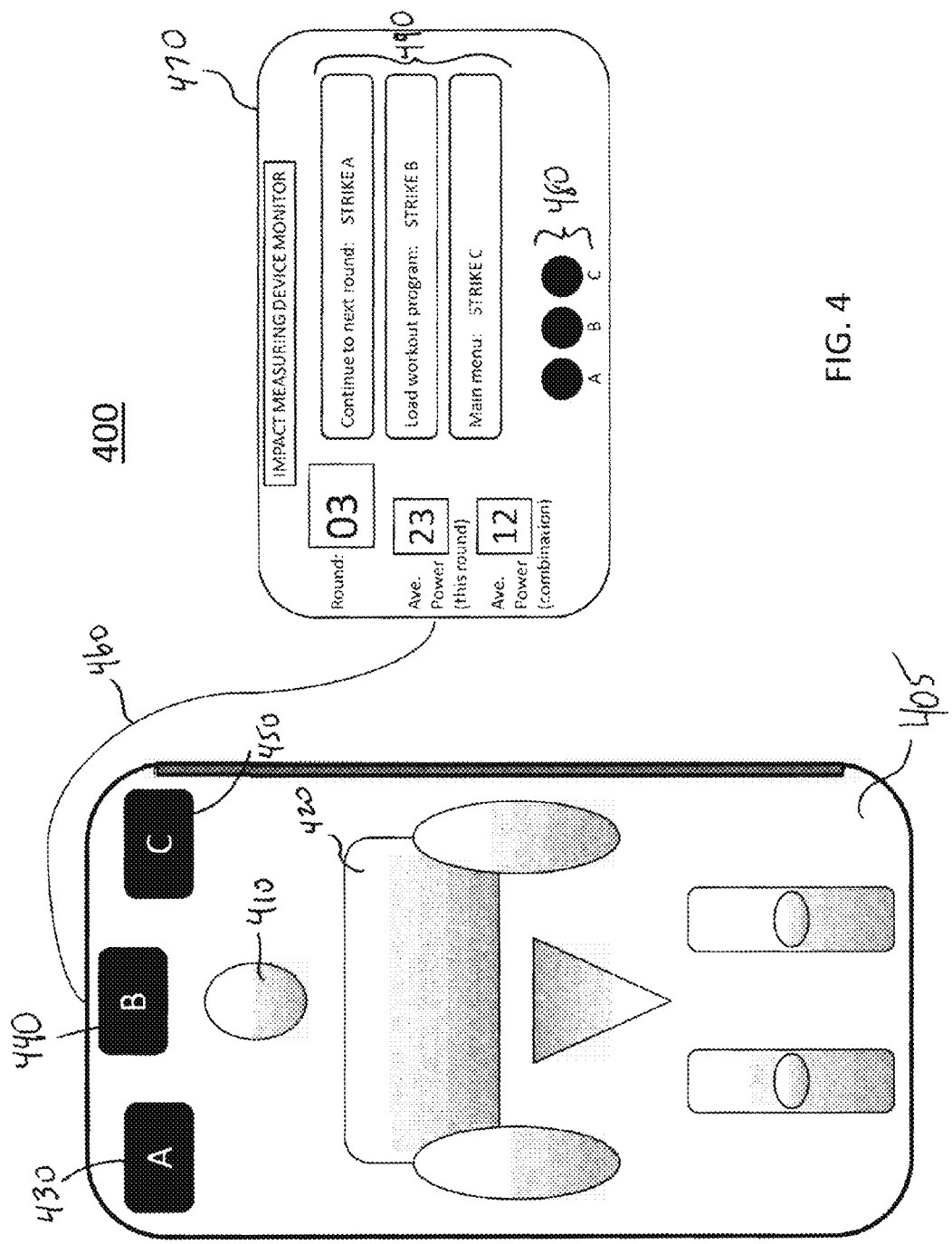
FIG. 4 is a system for generating, analyzing, and displaying impact force data, according to one embodiment.

Referring now to FIG. 4, an IFFS 400 is shown, according to one embodiment. Similar to the IFFS 100 shown in FIG. 1, this IFFS 400 includes a mat 405 having one or more integral sensors, e.g., head sensor 410, torso sensor 420, etc., similar to that previously described. Program control sensor pads 430, 440, and 450 are integrated into the mat 405 to enable functional control of IFFS software, e.g., via the display screen 470. Line 460 in FIG. 4 serves to illustrate data communication between mat sensors (e.g., sensors 410 and 420, meant for striking, and program control sensor pads 430, 440, 450 described above) and the display output. A control module (not shown in FIG. 4) having the same or similar functionality to that described above with respect to FIG. 3 can be used for receiving sensor input and providing data output to the display 470 as previously described. Similarly, any electronic communications protocol known in the art can be used for sending data between the mat 405 sensors, control module(s), and the display 470.

The display 470 in FIG. 4 shows an exemplary IFFS software menu 490. The menu 490 shows an illustrative prompt, asking the user to choose between several options: continuing a workout by progressing to another round, loading a preconfigured workout program, or displaying the main menu of the software program. Beside each option the prompt includes instructions to strike "A," "B," or "C" to make the selection. To choose one of the options, the user can select one of A, B, or C (480) on the display 470, e.g., by touching the screen in a touch-screen application, or the user can strike the corresponding A (430), B (440), or C (450) program control sensor pad on the mat 405 to effect the same selection. Such functionality offers practitioners who wear large gloves the ability to easily navigate menus, make selections, and perform other software input functions without having to doff their gear. The large, spaced pads can also reduce the likelihood of inadvertently activating two or more inputs simultaneously, if, e.g., a user were to try to make a selection on the screen 470 using large gloves. It will be understood that the number of mat program control sensor pads can be chosen according to user preference and so as to provide an intuitive and useful interface to programmatic features of an IFFS.

Figure 5:
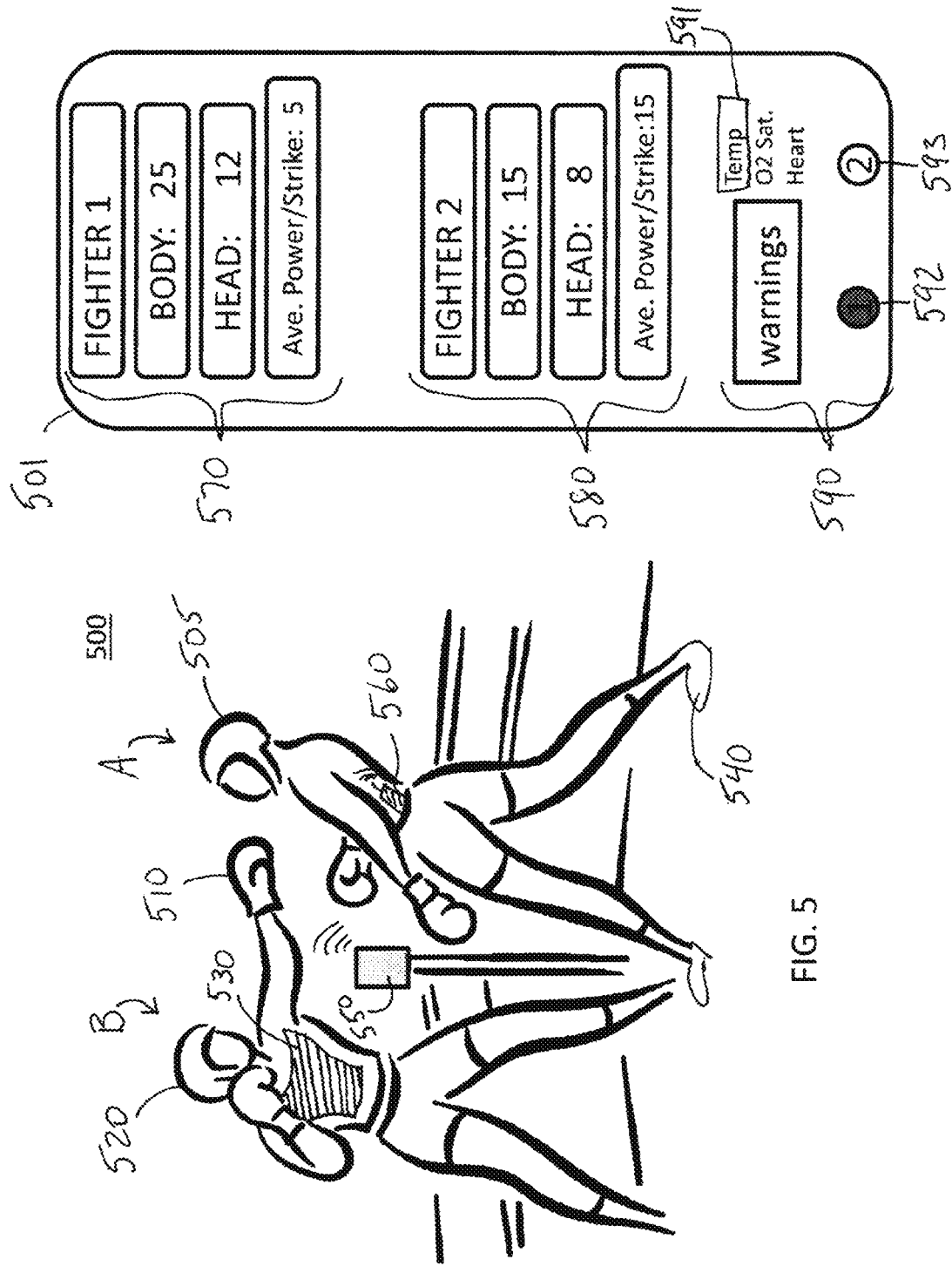
FIG. 5 is a system for generating, analyzing, and displaying impact force data, and an exemplary display screen, according to one embodiment.

Referring now to FIG. 5, several aspects of an impact feedback system 500 are shown, according to one embodiment. In this embodiment, impact sensors similar to those described above can be placed within sporting equipment and optionally on the person of one or more of the participants. FIG. 5 shows two opponents sparring, referred to in the figure as person A and person B. Person A is wearing a helmet 505 that includes a sensor (not shown in FIG. 5) similar to those sensors described above. Person A is also wearing footwear 540 that incorporates a sensor. Person B is wearing gloves 510, 520 similar to those used by boxers that also includes sensors attached therein. Furthermore, person B is wearing a body sensor 530, which is a sensor capable of sensing impact. The body sensor 530 can be incorporated into a vest or other garment, or, in some embodiments, can be worn directly on a person's skin through the use of light adhesives or similar methods. The body sensor 530 can include multiple sub-sensors, e.g., strips of individual sensors aligned in parallel to provide the ability of spatially resolving strikes to certain areas of the sensor 530 (e.g., right side, left side, etc.). It will be understood that any of the above-described sensors or other alternatives can be worn on either person A or person B in this example.

In this and all other embodiments described herein, sensors can be placed on the inside, outside, or within any part of the above-described gear, bags, mats, striking surfaces, and equivalents known in the art. For example, a sensor can be incorporated into the inside of a boxing glove 510, 520, i.e., within the part of the glove containing padding or other materials that serves to protect the user's hands from injury. In another example, a helmet (e.g., helmet 505) can include an exterior-mounted sensor; or, in some embodiments, a sensor can be placed on the interior portion of the shell, such that when worn, the sensor is placed between the user's forehead and the front part of the helmet shell.

The sensors (e.g., sensors 505, 510, 530, 540) can transmit impact force data to a transmitter 560 which can be, e.g., worn on the user. In the embodiment of FIG. 5, the transmitter 560 transmits the user-specific sensor impact force data to a receiving unit 550 situated on the periphery of the boxing ring. The receiving unit 550 can route the user-specific sensor impact force data to a sensor data receiver (not shown in FIG. 5) similar to that described with respect to FIG. 3. In some embodiments, program control sensors similar to those described with respect to FIG. 4 can be integrated within sporting equipment, to provide users the ability to control IFFS program functions from their sporting equipment, e.g., a pair of boxing gloves.

In this embodiment, the sensors (e.g., sensors 505, 510, 530, 540) are capable of transmitting impact force data wirelessly to the receiving unit 560; in some embodiments, the sensors are wired directly to the receiving unit 560 through the use of electronic leads or similar connections. In cases where the sensors transmit information wirelessly, the receiving unit 550 can be configured to receive user-specific sensor impact force data without the use of a transmitter (e.g., transmitter 560).

Similar to the embodiments of FIG. 1A, the sensor data receiver can be part of a control module (not shown in FIG. 5) that can show impact force data on a display 501. FIG. 5 shows a screen snapshot 501 of exemplary force impact data corresponding to the sparring match between person A and person B. In this example, the screen snapshot 501 includes grouped impact force data (570) for fighter A and grouped impact force data (580) for fighter B. As shown, the grouped impact data for both fighters includes the number of head shots, body shots, and average power per strike. These data can originate from the sensors (e.g., sensors 505, 510, 530, 540) and can be correlated to the performance of each respective fighter; such calculations can be performed by a control module similar to that described with respect to FIG. 3.

In one embodiment of an IFFS, physiological data of a user can be monitored. A user of an IFFS can wear one or more devices that measure physiological data such as the user's vital signs (blood pressure, body temperature, heart rate, oxygen saturation, etc.). Those data can be transmitted with sensor data and processed by the control module to provide real-time monitoring of a user's physiology, stamina, or other aspects. The bottom portion of the screen snapshot 501 in FIG. 5 includes a "warnings" section 590 for this or other purposes. A user can program certain physiological threshold limits, such as a heart rate threshold or a temperature threshold that will trigger an alert to be shown on the warnings section 590 of the display 501, so that the contestants can stop the match until safely able to continue.

Consider the following example where person A exceeds a pre-selected body temperature threshold. Temperature data (i.e., physiological data) sent by a physiological sensor on person A is received by the control module (not shown in FIG. 5); the control module provides substantially real-time monitoring of sensor data, and the above-threshold value of person A's temperature triggers a warning. The control module causes the warnings section temp indicator 591 to illuminate, e.g., through the use of bright, light emitting diodes. The "1" (592) or "2" (593) indicator can also illuminate to indicate which of the contestants (e.g., person A or person B in FIG. 5) triggered the event. In some embodiments an audible warning signal can sound concurrently with the visual indicator. For example, the display 501 can include an integrated speaker that produces a warning sound when a threshold event or other event occurs. Other events can include signaling the end of a match round; attaining a performance goal such as successfully landing a pre-determined number of head shots per round or sustaining a certain impact force per strike over a period of time.

Figure 6:
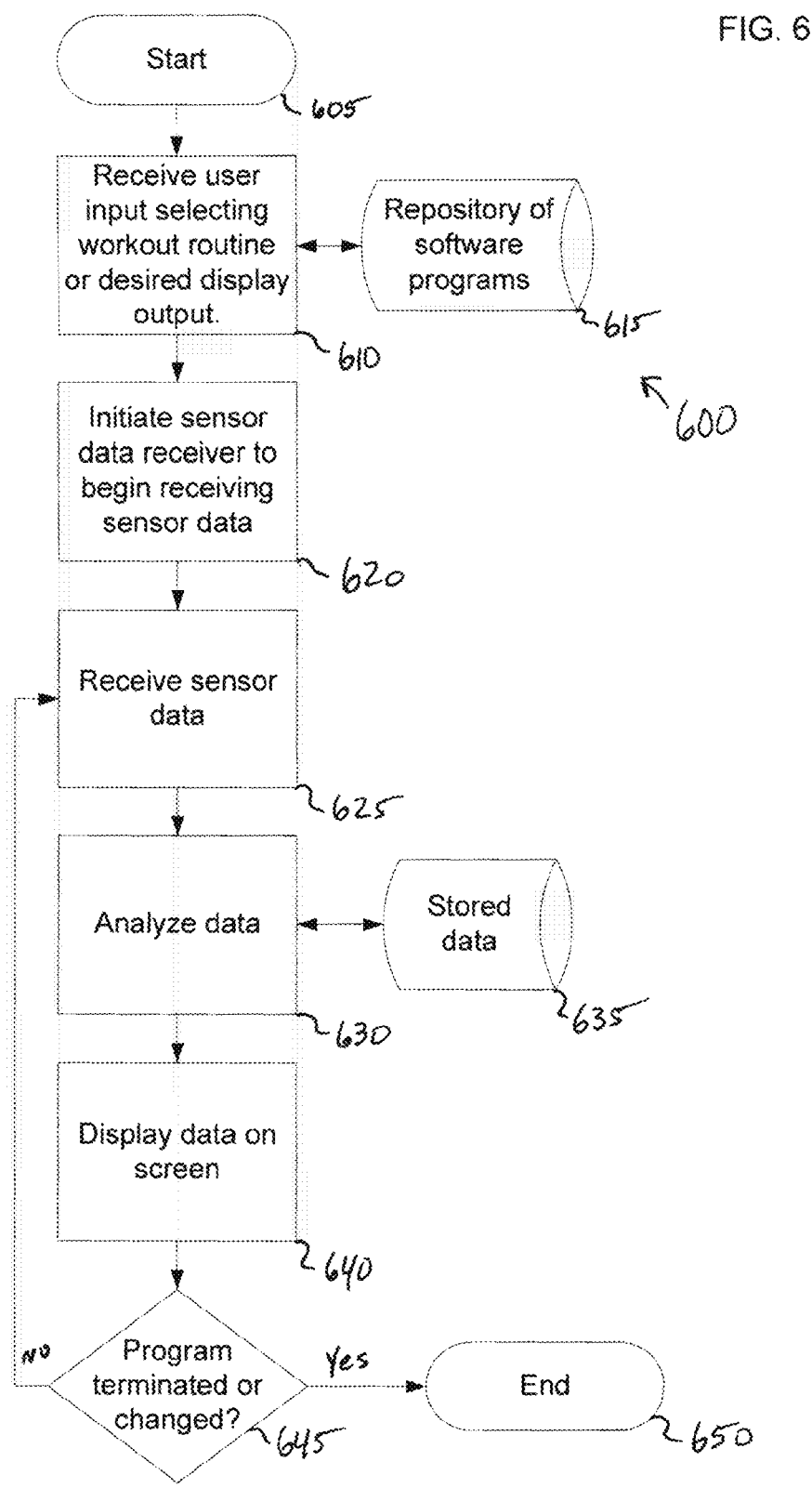
FIG. 6 is a flow chart showing steps for generating, analyzing, and displaying impact force data, according to one embodiment.

Referring now to FIG. 6, a flow diagram 600 is shown, according to one embodiment. The flow diagram 600 shows one exemplary method for receiving impact force data in an IFFS system from a sensor, analyzing the data, and displaying the data. The exemplary method can be executed by, e.g., a control module of the type described herein, e.g., control module 300 described in FIG. 3.

The method starts (605) when the control module receives a user input selecting a workout routine or a desired display output (box 610). This step can be accomplished by, e.g., the user providing power to an IFFS system, e.g., by turning on a power switch on the display panel, and selecting from a menu of software-driven commands. The software menu can allow the user to select, e.g., a pre-loaded workout routine, such as one that allows a user to practice timed combination punches, kicks, and the like. Preloaded workout routines can be stored as software programs in a computer repository, such as a hard drive, memory, flash drive, etc. (615). Alternatively, the user may wish to simply have the IFFS count, record, and analyze a "free-form" workout, where the user strikes IFFS sensors at will, and the punches, kicks, and forces of each are collected for later inspection or analysis. In such instance access to stored software and/or configuration files may not be necessary. In yet another embodiment, a software program can be loaded from the repository 615 that causes commands or targets to be called out to the user, such as "head!" "torso!" "knee!" etc. These commands or targets can prompt the user to strike sensor pads located on, for example, the corresponding anatomy of a mat as described herein, or on an opponent. The control module can monitor for a strike to the appropriate sensor and provide visual or auditory feedback to the user relating to speed, accuracy, and other measurables.

At step 620, the control module initiates the sensor data receiver. The initiation process can include clearing any old data files, cache, or memory, including memory buffers that may have old data contained therein. The initiation process can also include providing power to sensors, or initiating a power-up sequence for one or more sensors. If necessary, disk space or memory can be allocated for receiving streaming data from the sensors at this step.

At step 625, sensor data from one or more sensors is received by the sensor data receiver. In some cases, the sensor data can include information that identifies the sensor sending the data; for example, data packets may be sent from the sensor to the receiver having a header that uniquely identifies the sending sensor from other sensors that may be transmitting at the same, or substantially the same time.

At step 630 the sensor data is analyzed. In some cases the analysis process may be to correlate a received sensor force measurement with a timestamp; in other cases the analysis process may be more involved. In cases where sensor data is streaming to the control module on a real-time basis, the analysis procedure may involve analyzing chunks of data over a given amount of time. For example, in order to compute average striking power, data over ten second intervals can be analyzed; these results can then be used by other components of the control module to perform further analysis or display the results. In some embodiments, raw or analyzed data can be stored (step 635) locally, e.g., in memory or on a hard drive, permitting analysis of historical data in some embodiments.

Data caching is another data storage process that can lessen the computing burden on a processor or aid in analyzing large amounts of data, e.g., when multiple sensors are sending data simultaneously.

At step 640 the control module sends the analyzed sensor data and other information to the display. "Other information" can include, for example, aspects of a workout routine or other IFFS functionality as described herein, which may be dependent on the particular software being used. The frequency with which the display is updated can be configured as described above. For example, the display can be programmed to update every 10 seconds; alternatively, the display can receive streaming data where the information is presented to the user in substantially "real" time.

Step 645 is a decision that can arise, e.g., when a user reaches the end of a pre-configured workout or the user has chosen to end a workout early. Step 645 can manifest in a display prompt asking, e.g., whether the user wishes to load another, pre-configured workout routine, rest for a period of time, load new variables into a program, or other queries. If the user chooses to terminate a program, the control module can cease to continue analyzing impact force data and may return to a "home screen" state where a user can begin a new routine. Alternatively, the user may continue their practice wherein the process returns to step 625.

Figure 7:
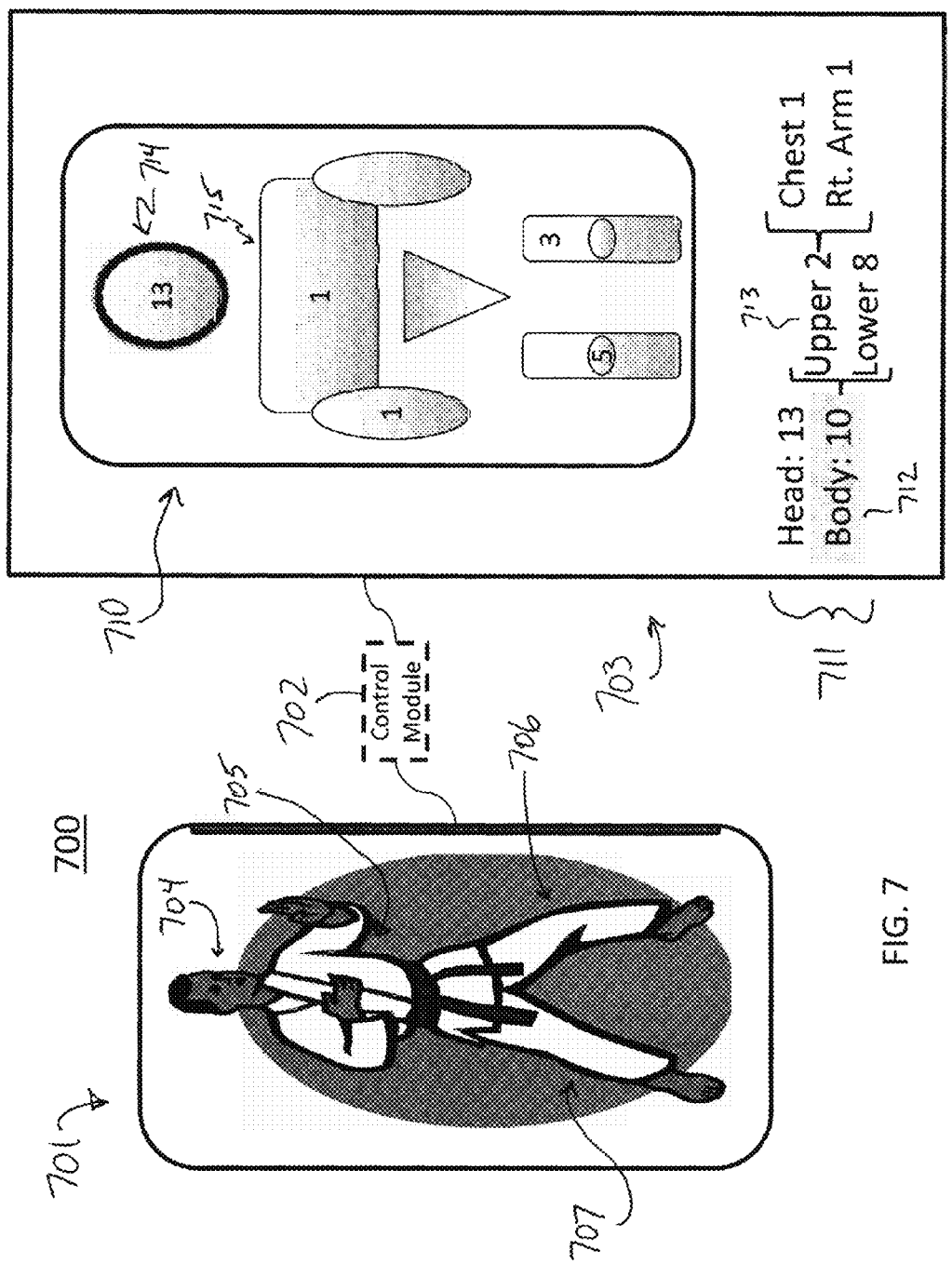
FIG. 7 is a system for generating, analyzing, and displaying impact force data, and an exemplary display screen, according to one embodiment.

Referring now to FIG. 7, an IFFS system 700 is shown, according to one embodiment. Similar to the embodiments described above, the IFFS system 700 shown includes a striking surface 701 in data communication with a control module 702, which itself is in data-transfer communication with a display 703. In this embodiment, substantially the entire striking surface 701 is an impact sensor. It will be understood, however, that the striking surface 701 in this IFFS system 700 can be similar to those already described above. The impact sensor can have segregated zones which, in this embodiment, can combine to form substantially seamless shapes corresponding to the form of a human body, e.g., regions corresponding to a head (704), chest (705), left leg (706), and right leg (707) respectively. The impact sensor can be configured as a mapped sensor, meaning that the location of a strike or blow to the sensor can be determined on a defined coordinate system, e.g., a Cartesian coordinate system defined for the striking surface 701. In some embodiments, the striking surface 701 can include marking indicia, e.g., printed outlines of the simulated body parts as shown in FIG. 7.

In one example, the control module 702 is equivalent, or substantially equivalent to control module 300 described with respect to FIG. 3, and furthermore can include programmatic capability to determine coordinates, e.g., an x-y coordinate pair, of a strike to the striking surface 701. The coordinates of the strike can be compared to known coordinates of the body part indicia on the striking surface 701. In some embodiments, the locations of the body parts on the striking surface 701 can be stored as one or more arrays of coordinate data that combine to form regions corresponding to the body part indicia, e.g., head 704 and right leg 707. Comparison between the coordinates of a detected strike on the striking surface 701 and the stored coordinate data provides the capability to map the location of a strike on the striking surface 701; a history of such strikes can be stored for analysis purposes.

The control module 702 is capable of receiving impact force data from the striking surface 701, processing the impact force data, and providing an output to the display 703 similarly to that described above, e.g., with respect to FIG. 1A. In this embodiment, the display 703 shows a representation of the simulated body parts of the striking surface 701. Although FIG. 7 shows "block" features of the corresponding body parts printed on the striking surface 701, it will be understood that the display can show a substantially similar image as that shown on the striking surface 701 and include the same functionality as described next.

In this embodiment and others, the control module 702 is capable of sending display data to the display 703 to show real-time and historical impact force data. In the embodiment of FIG. 7, the body display 710 shows the total number of strikes delivered to various regions, e.g., the head region (704 on the striking surface 701) has received thirteen strikes; similarly, the chest region (705 on the striking surface) has received 1 strike. The body display 710 can show total impacts to an area (as shown in FIG. 7) or any other raw or calculated impact force data. For example, and without limitation, the body display 710 can show the average striking power of a strike to the head region; the body display 710 can similarly show the force delivered by the last strike to a leg region, etc.

Real-time and historical data can be shown on display 703 and can further be controlled by touch-screen interaction. In the exemplary embodiment shown, data area 711 shows a head and body count, showing the number of strikes delivered to the head (thirteen) and the body (ten) respectively. Such a count can represent, for example, the accumulated shot count from the beginning of a work-out round.

In one embodiment, touching the display 703 in a selected area can control which data is shown in the data area 711. For example, the head count shown in the data area 711 of FIG. 7 can be caused to appear by touching the head region 714 of the body display 710. In another example, the total number of body shots accumulated for all body parts, e.g., torso, arms, legs, etc., can be caused to appear by selecting multiple body parts, or, in a preferred embodiment, by performing a finger swipe against the body display 710 in a substantially diagonal direction to multiply select a plurality of body parts.

Data shown on the display 703 can be selected so as to drill down into finer detail. For example, in the embodiment of FIG. 7, the user has selected a "body shots" area 712 (as indicated by the gray box) which selection causes an expansion of body shot data to be adjacently displayed. In this example, the total number of body shots includes two shots to the upper body region, and eight shots to the lower body region of the striking surface 701, as shown. The user may further drill down into the "upper" body shot data by selecting the "upper" data area 713; this causes a breakdown of shots received to the upper body to be displayed, namely, one to the chest and one to the right arm. It will be understood that the IFFS software can be programmed to allow drilling down into any raw or calculated data.

Still referring to FIG. 7, in this and other embodiments, the body display 710 of the display 703 can indicate in substantially real time a corresponding portion of the striking surface 701 that has been hit. FIG. 7 shows head region 714 having a "halo" effect compared to other body parts, indicating that the head portion (704) of the striking surface 701 was just hit. Visual indicia for this purpose can include, without limitation, changes in color, brightness, contrast, display of words and images, and other indicia.

In this an all other embodiments, selecting data portions (e.g., selecting the "body shots" 712 or "upper" body shots area 713) can be accomplished through touch-screen, toggle switch, button control, keyboard, mouse, and any other display selection method known in the art. It will be understood that user interaction with a display in this and all other embodiments can cause programmatic selection and execution of software and hardware instructions within a control module, e.g., control module 702, that can be integral with the display or operating remotely and linked by data communication methods described herein and known in the art.

Figure 8A:
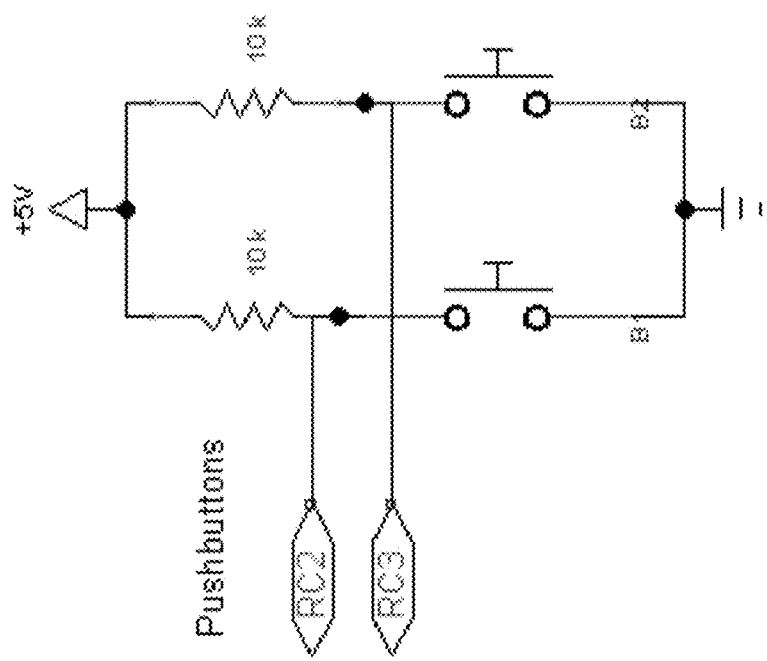
FIG. 8A shows exemplary computer circuitry for a push-button control, according to one embodiment.
Figure 8B:
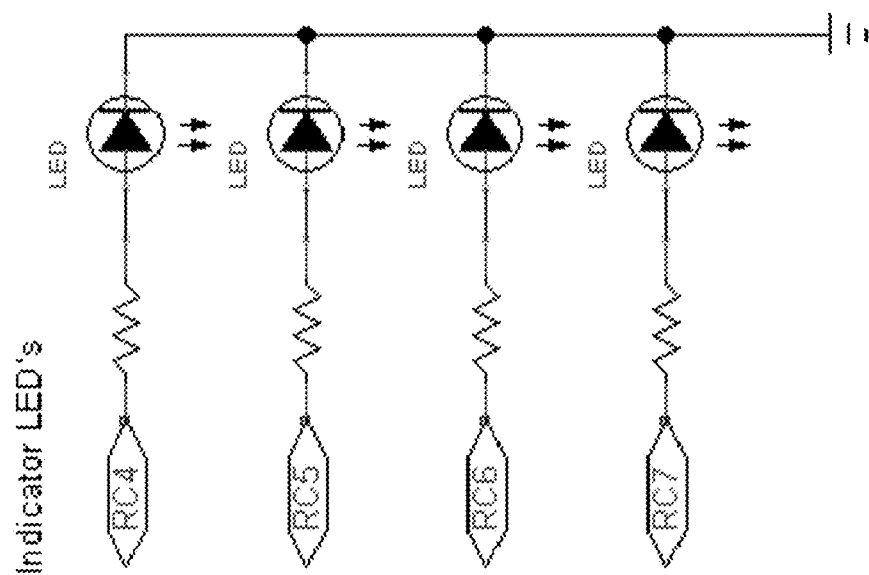
FIG. 8B shows exemplary computer circuitry for an indicator LED, according to one embodiment.
Figure 8C:
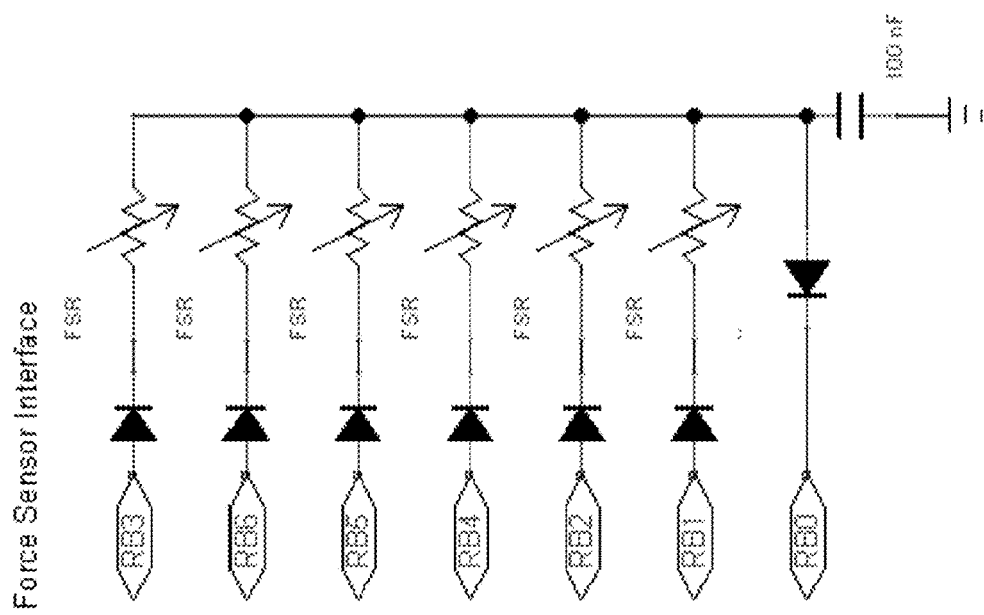
FIG. 8C shows exemplary computer circuitry for an force sensor interface, according to one embodiment.
Figure 8D:
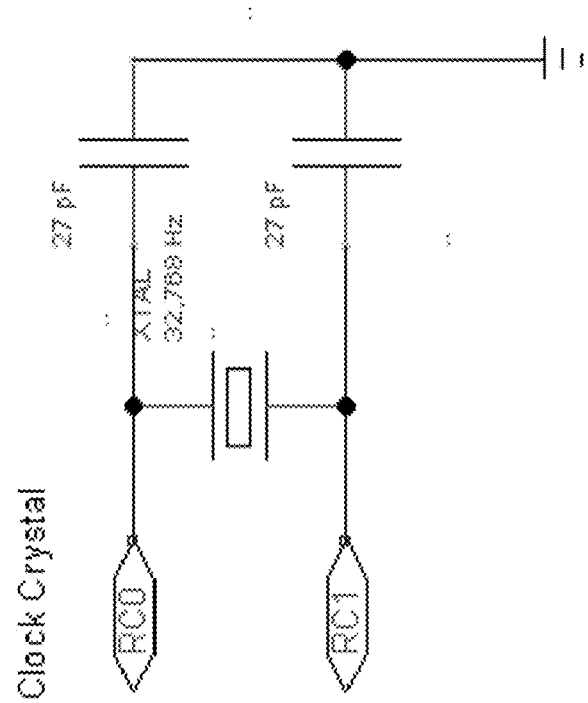
FIG. 8D shows an exemplary timing circuit, according to one embodiment.
Figure 8E:
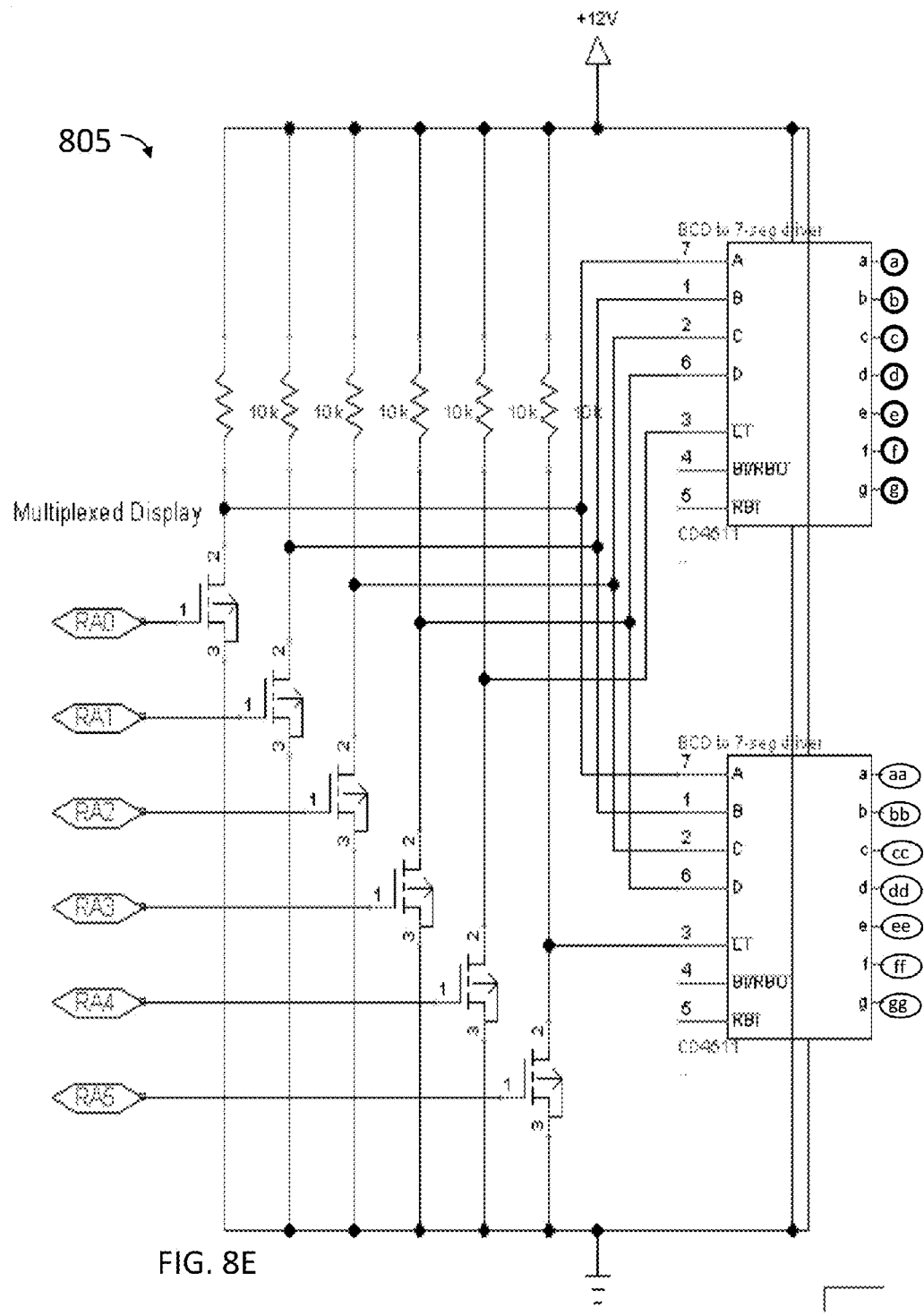
FIG. 8E shows exemplary circuitry for displaying alphanumeric output, according to one embodiment.
Figure 8E:
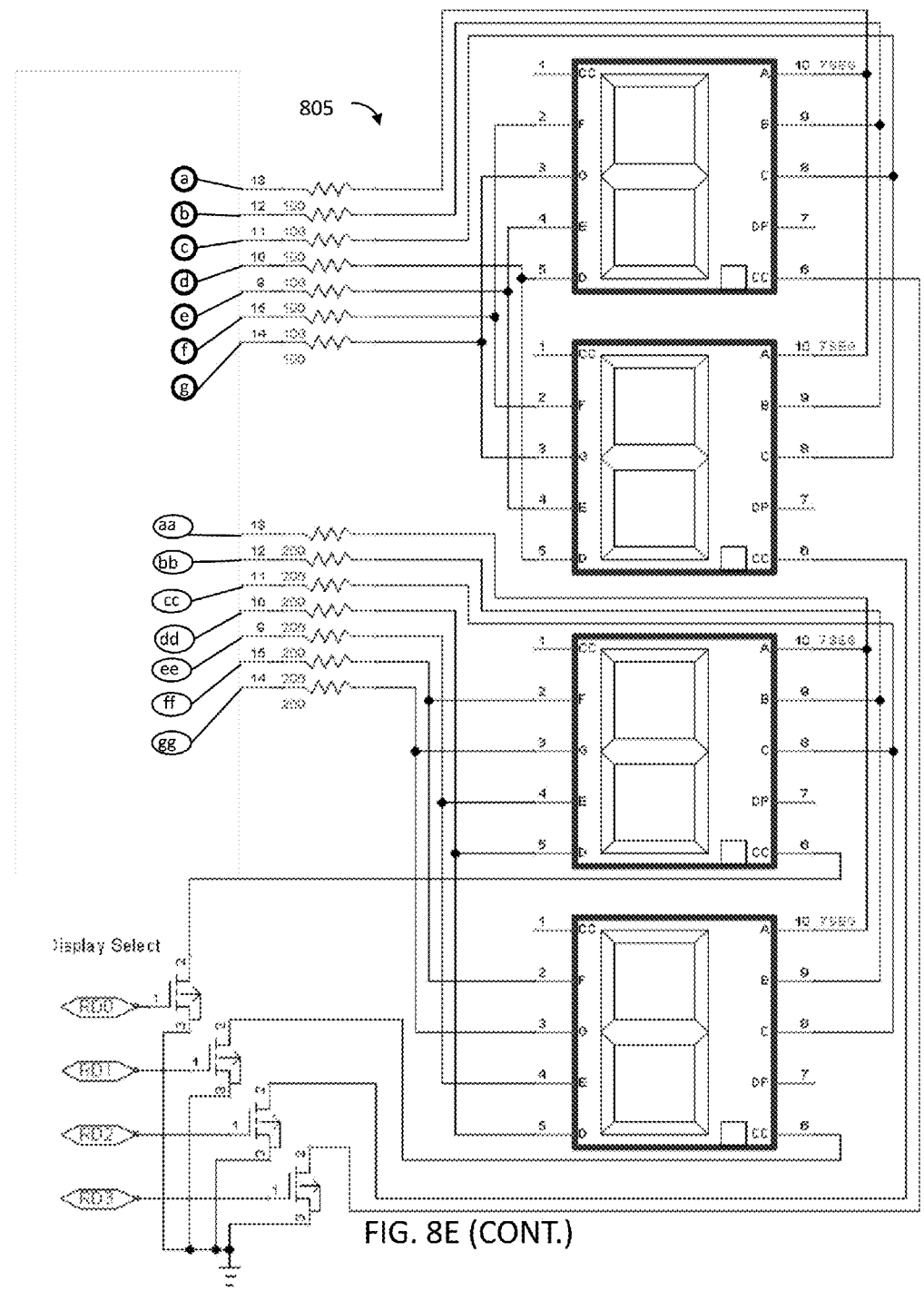

Referring now to FIGS. 8A-E, circuit diagrams for some of the components of the control modules or displays described above are shown, according to one embodiment. Specifically, pushbutton controls, e.g., those controls as described above that can control software, firmware, or hardware instructions can be embodied in the pushbutton circuit 801 shown in FIG. 8A. Indicators, e.g., light emitting diodes (LED's) used in display panels of the type described above (e.g., indicators 295 in FIG. 2) can be implemented by the indicator circuit 802 shown in FIG. 8B. A force sensor interface can be embodied in a force sensing interface circuit 803 as shown in FIG. 8C; exemplary force-sensing resistors include the FSR family of force sensing resistors sold by Interlink Electronics, Camarillo, Calif., 93012; an exemplary diode is an IN914 diode, although other diodes may be used. In any embodiment, a load cell transducer can be used for measuring force and converting that force measurement into a measurable electrical output. FIG. 8D shows a clock circuit 804 that can be used in timing and other functions that will be apparent to those skilled in the art. Display circuit 805 (FIG. 8E) shows one embodiment of a multiplexed display and multiplexed display selectors; the 2N7000 MOSFET transistor is an exemplary transistor that can be used in the embodiment shown. Those skilled in the art will recognize that various substitutions and alternate circuit configurations can be made while retaining the same or similar functionality as described. In addition, the way in which the various circuit diagrams shown in FIGS. 8A-8E are connected to form an interoperable system can be selected according to circuit printing requirements or parameters; or can be chosen to achieve maximum operability in an end product.

In general, an IFFS can be controlled by voice commands. For example, speakers and microphones can be integrated into the IFFS control system to allow a user to execute software, firmware, or hardware instructions so that the IFFS program can be operated "hands-free." In one example, when a user is reaching the end of a work-out session, the IFFS can prompt the user to continue by broadcasting audio over a speaker system. The user can respond by voice, e.g., by saying "OK" or "go to next round" which would cause the IFFS to load and execute another workout regimen. In some embodiments, voices of well-known persons can be used when broadcasting messages to the user. For example, the voice of, or a voice resembling Mike Tyson can be used. Voice control and voice recognition software and hardware is known in the art and can be implemented in any IFFS system. Exemplary voice control/recognition software includes the Dragon software suite produced by Nuance Communications, Burlington, Mass. 01803.

A number of illustrative embodiments have been described. Nevertheless, it will be understood that various modifications may be made without departing from the spirit and scope of the various embodiments presented herein. For example, sensors can be integrated into sporting equipment during manufacture thereof, including but not limited to gloves, pads, mats, covers, heavy bags, shells that wrap around heavy bags, focus pads and mitts, body vests, etc. Any of the described embodiments can be configured to include data capture and visualization of impacts in or on pre-determined strike zones. For example, a body vest can include segregated strike zones, and the vest can include the necessary electronic components to transmit impact force data within a segregated strike zone to a control module. While many of the described embodiments include sensors housed within mats, it will be understood that IFFS sensors can be integrated in any piece of sporting or protective equipment, clothing, and other articles capable of physically supporting or enclosing the device. Accordingly, other embodiments are within the scope of the following claims.

What is claimed is:

1. A system, comprising:
    a mat configured to be mounted to a heavy bag comprising one or more flexible impact sensors arranged so as to imitate a human physiological form;
    an electronic control module configured in part to receive impact sensor signals corresponding with a strike to said one or more flexible impact sensors and display a corresponding impact value having units of force on a display device;
    wherein said electronic control module is configured to receive and store one or more user preferences for displaying said impact value, and further configured to store and execute logic instructions for effectuating a pre-defined boxing or martial arts exercise routine;
    wherein each of said one or more flexible impact sensors individually transmits an impact sensor signal only when struck directly, and, for each individual impact sensor, each of said impact sensor signals is substantially devoid of impact forces imparted outside of said each individual impact sensor; and
    wherein said control module is further configured such that an impact sensor signal can be used for controlling said electronic control module.

2. The system of claim 1, wherein said flexible impact sensor is a force-sensing resistor.

3. The system of claim 1, wherein said unit of force is Newtons.

4. The system of claim 1, wherein said flexible impact sensor is configured to mimic a human anatomical feature.

5. The system of claim 1, further comprising an attenuation pad disposed between two of said flexible impact sensors, wherein said attenuation pad provides a calibrated force-reduction factor.

6. The system of claim 5, wherein said control module is configured to apply said calibrated force reduction factor to said impact value.

7. The system of claim 1, wherein one or more of said flexible impact sensors comprises a mapped array of smaller flexible impact sensors configured to correlate to sub-features of said human physiological form.

8. The system of claim 1, wherein said electronic control module is configured to prompt a user for a control input, and said input is received by said electronic control module in return by a user-generated impact sensor signal.

9. The system of claim 8, wherein said control input is a query comprising a plurality of optional choice answers, each of said optional choice answers is mapped to a particular one of said flexible impact sensors, and user selection of one of said choices is achieved by generating an impact sensor signal from one of said flexible impact sensors.

10. The system of claim 8, wherein said control input is a query comprising a plurality of optional choice answers, and a user-selection of one of said answers is selectable by tapping one of said flexible impact sensors a number of times until the desired answer is selected.

11. The system of claim 1, wherein said logic instructions for effectuating a pre-defined boxing or martial arts exercise routine comprise logic for causing a pre-defined sequence of target strike areas to be communicated to a user by visual cues, audio cues, or both, through one or more lights, speakers, or both in signal communication with said control module.

12. The system of claim 11, wherein said control module is further configured to receive a measured physiological parameter of a user from a user-wearable measurement device in signal communication with said control module.

13. The system of claim 11, wherein said control module further comprises an analysis module configured to compare said communicated pre-defined sequence of target strikes to corresponding actual strikes delivered by said user to calculate a correlation value.

14. The system of claim 13, wherein said control module is further configured to receive a measured physiological parameter of a user from a user-wearable measurement device in signal communication with said control module; and
    wherein said correlation value incorporates said measured physiological parameter.

15. The system of claim 14, wherein said exercise routine comprises boxing rounds, and said correlation value is computed for each of said rounds.

16. The system of claim 1, wherein said flexible impact sensor is configured to mimic a human torso, and wherein said flexible impact sensor comprises defined, segregated strike zones corresponding to individual anatomical torso features; and wherein said control module is configured to correlate a strike to one of said individual anatomical torso features through use of a defined coordinate system that defines said segregated strike zones.

17. The system of claim 16, wherein said individual anatomical torso feature is a head, neck, left arm, right arm, chest, or abdomen.

18. The system of claim 1, wherein said control module is configured to record impact sensor signals over a period of time, and further configured to allow a user to visualize strike statistics correlating to one or more of said flexible impact sensors on said display device in an analysis mode by touching a selected one of said flexible impact sensors.

19. A method for communicating with a control module configured for effectuating a pre-defined boxing or martial arts exercise routine, comprising:
    providing a mat configured to be mounted to a heavy bag, the mat comprising at least one flexible impact sensor in signal communication with said control module, wherein said flexible impact sensor is configured in the shape of a human anatomy;
    providing logic instructions for effectuating said pre-defined boxing or martial arts exercise routine by said control module;
    wherein said control module is configured to receive an impact signal from said impact sensor correlated with a strike to said impact sensor and display a strike force value on a display device if said strike is delivered during said exercise routine; and further wherein said control module is configured such that impact sensor signals received by said control module outside of said pre-defined boxing or martial arts exercise routine control one or more executable features of said routine.

20. A strike-practice system, comprising:
    a mat configured to be mounted to a heavy bag comprising a plurality of flexible force-sensing resistors arranged so as to mimic portions of a human anatomy and configured to wirelessly transmit an impact signal to an electronic control module;
    a control module processor;
    a control module memory;
    a control module data store for storing logic for carrying out a pre-defined boxing or martial arts exercise routine, wherein said routine comprises visual or audio commands engendering a user to strike said mimicked portions of said human anatomy according to a pre-defined sequence;

wherein said control module is configured for receiving user input for starting, stopping, or modifying said pre-defined boxing or martial arts exercise routine; and wherein said receiving user input for starting, stopping, or modifying said pre-defined boxing or martial arts exercise routine comprises receiving an impact signal from one of said plurality of said flexible force-sensing resistors.

* * * * *